United States Patent [19]

Metivier et al.

[11] Patent Number: 5,756,853
[45] Date of Patent: May 26, 1998

[54] PROCESS FOR THE PREPARATION OF A SUBSTITUTED 4-HYDROXYBENZALDEHYDE

[75] Inventors: Pascal Metivier, Sainte Foy Les Lyon; Isabelle Jouve, Genas; Christian Maliverney, Lyons, all of France

[73] Assignee: Rhone-Poulenc Chimie, Courbevoie, France

[21] Appl. No.: 722,210

[22] PCT Filed: Feb. 14, 1996

[86] PCT No.: PCT/FR96/00241

§ 371 Date: Oct. 16, 1996

§ 102(e) Date: Oct. 16, 1996

[87] PCT Pub. No.: WO96/26175

PCT Pub. Date: Aug. 29, 1996

[30] Foreign Application Priority Data

Feb. 20, 1995 [FR] France ................... 95/01926

[51] Int. Cl.$^6$ .................................................. C07C 45/65
[52] U.S. Cl. .......................... 568/433; 562/424; 562/406; 562/475; 562/463
[58] Field of Search .......................... 562/424, 475, 562/463, 403, 406; 568/433; 508/433

[56] References Cited

U.S. PATENT DOCUMENTS

| | | | |
|---|---|---|---|
| 4,036,873 | 7/1977 | Huffman | 562/424 |
| 4,996,354 | 2/1991 | Neumann et al. | 562/424 |

FOREIGN PATENT DOCUMENTS

| | | |
|---|---|---|
| 51381 | 4/1889 | Germany . |
| 71162 | 7/1892 | Germany . |
| 72600 | 3/1893 | Germany . |

OTHER PUBLICATIONS

Arch. Microbiol. (amiccw, 03028933); 79; vol.121 (1); pp. 23–28, Kyoto Univ.; Wood Res. Inst.; Uji; Japan, XP002003065 Ohta M et al; "Microbial degradation of dehydrodiconiferyl alcolol, a lignin substructure model" see page 26.

*Primary Examiner*—James H. Reamer
*Attorney, Agent, or Firm*—Katherine L. Carleton

[57] ABSTRACT

The subject of the present invention is a process for the preparation of a 4-hydroxybenzaldehyde carrying at least one substituent in the position ortho to the OH group.

It more particularly relates to the preparation of 3-methoxy-4-hydroxybenzaldehyde and of 3-ethoxy-4-hydroxybenzaldehyde.

The process for the preparation of a substituted 4-hydroxybenzaldehyde, substituted at least in the 3 position by an alkoxy group, is characterized in that it comprises subjecting a substituted phenol compound, substituted at least in the 2 position by an alkoxy group and in which the 4 and 6 positions are free, to a first stage of carboxylation in the 6 position, then to a stage of hydroxymethylation in the 4 position, followed by a stage of oxidation of the hydroxymethyl group to a formyl group, and finally to a last decarboxylation stage.

39 Claims, No Drawings

PROCESS FOR THE PREPARATION OF A SUBSTITUTED 4-HYDROXYBENZALDEHYDE

The subject of the present invention is a process for the preparation of a 4-hydroxybenzaldehyde carrying at least one substituent in the position ortho to the OH group.

It more particularly relates to the preparation of 3-methoxy-4-hydroxybenzaldehyde and of 3-ethoxy-4-hydroxybenzaldehyde, known respectively as "vanillin" and "ethyl vanillin".

Vanillin is obtained mainly from natural sources such as lignin but a part is prepared chemically.

Many preparation methods are described in the literature [Kirk-Othmer, Encyclopedia of Chemical Technology, 23, p. 1710, 3rd edition] and a number of them start from guaiacol or 2-methoxyphenol.

Thus, mention may be made of the preparation of vanillin by reaction of guaiacol and glyoxylic acid, oxidation of the condensate by air and then release of the vanillin from the reaction mixture by acidification. The disadvantage from which this process suffers is that it uses glyoxylic acid, which is an expensive reactant.

Another access route to vanillin according to the Reimer-Tiemann reaction comprises the reaction of guaiacol and chloroform in the presence of potassium hydroxide. The formation of resin is a disadvantage of this method of preparation.

According to the Gatterman reaction, vanillin is synthesized by reaction of hydrocyanic acid with guaiacol, in the presence of hydrochloric acid. In addition to the use of a reactant which is difficult to handle, this process has the disadvantage of not being selective, because the vanillin is accompanied by isovanillin and o-vanillin.

A major difficulty present in the synthesis of vanillin is selectively to attach a formyl group to guaiacol in the position para to the hydroxyl group.

Another problem to be solved is to provide a process which is competitive from an industrial viewpoint.

The present invention provides a new process which makes it possible to overcome the above-mentioned disadvantages while satisfying the requirements mentioned above.

A process for the preparation of a substituted 4-hydroxybenzaldehyde, substituted at least in the 3 position by an alkoxy group, has now been found, which constitutes the subject of the present invention, characterized in that it comprises subjecting a substituted phenol compound, substituted at least in the 2 position by an alkoxy group and in which the 4 and 6 positions are free, to a first stage of carboxylation in the 6 position, then to a stage of hydroxymethylation in the 4 position, followed by a stage of oxidation of the hydroxymethyl group to a formyl group, and finally to a last decarboxylation stage.

The process of the invention is based on the preparation of 2-hydroxybenzoic acids hydroxymethylated in the 5 position and substituted at least in the 3 position by an alkoxy group, which are used as intermediates in the synthesis of substituted 4-hydroxybenzaldehydes, substituted at least in the 3 position by an alkoxy group.

Another subject of the invention is the process for the oxidation of 2-hydroxybenzoic acids hydroxymethylated in the 5 position and substituted, at least in the 3 position by an alkoxy group, to the corresponding formylated 2-hydroxybenzoic acids.

The process of the invention is entirely well suited to the preparation of vanillin. Indeed, it makes it possible to selectively formylate guaiacol in the para position by successively carrying out carboxylation of guaiacol in the 6 position, hydroxymethylation followed by oxidation resulting in the formyl group in the 4 position and finally removal of the carboxyl group situated in the 6 position.

This process is not only selective but also very competitive from an industrial viewpoint because it uses inexpensive reactants.

Although the process of the invention is perfectly well suited to the use of guaiacol and of 2-ethoxyphenol, it is also suitable for other substituted phenol compounds.

"Substituted phenol compound" is understood to mean any aromatic compound in which the aromatic ring carries a hydroxyl group, an alkoxy group in the 2 position and other possible substituents and in which the 4 and 6 positions are free.

In the account which follows of the present invention, "aromatic" is understood to mean the conventional notion of aromaticity as defined in the literature, in particular by Jerry March, Advanced Organic Chemistry, 4th edition, John Wiley and Sons, 1992, pp. 40 et seq.

The invention very particularly applies, among substituted phenol compounds, to those which correspond to the general formula (I):

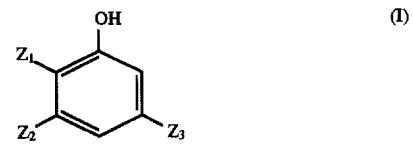

in the said formula (I):

$Z_1$ represents:
- a linear or branched alkoxy radical having from 1 to 12 carbon atoms, preferably from 1 to 4 carbon atoms, such as the methoxy, ethoxy, propoxy, isopropoxy, butoxy, isobutoxy, sec-butoxy and tert-butoxy radicals, $Z_2$ and $Z_3$, which are identical or different, represent a hydrogen atom or one of the following groups:
- a linear or branched alkyl radical having from 1 to 12 carbon atoms, preferably from 1 to 4 carbon atoms, such as methyl, ethyl, propyl, isopropyl, butyl, isobutyl, sec-butyl or tert-butyl,
- a linear or branched alkenyl radical having from 2 to 12 carbon atoms, preferably from 2 to 4 carbon atoms, such as vinyl or allyl,
- a linear or branched alkoxy radical having from 1 to 12 carbon atoms, preferably from 1 to 4 carbon atoms, such as the methoxy, ethoxy, propoxy, isopropoxy, butoxy, isobutoxy, sec-butoxy and tert-butoxy radicals,
- a phenyl radical,
- a halogen atom, preferably a fluorine, chlorine or bromine atom.

The present invention does not exclude the presence on the aromatic ring of substituents of a different nature, insofar as they do not interfere with the reactions of the process of the invention.

The present invention preferentially applies to the compounds of formula (I) in which $Z_1$ represents a linear or branched alkoxy radical having from 1 to 6 carbon atoms, preferably 1 to 4 carbon atoms, $Z_2$ and $Z_3$ representing a hydrogen atom.

Mention may be made, as preferred examples of substrates used in the process of the invention, of, inter alia, guaiacol and 2-ethoxyphenol.

In accordance with the process of the invention, the starting material is a substituted phenol compound which is preferentially a compound corresponding to the formula (I).

3

The reaction scheme of the process of the invention is given below to facilitate understanding of the account of the invention, without for all that binding the scope of the invention to the reaction scheme.

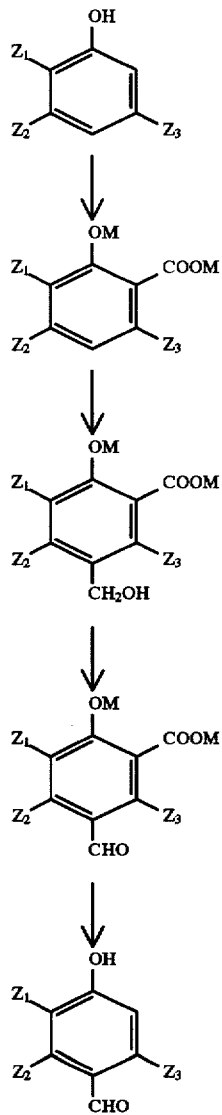

In the account which follows of the present invention, reference will be made to the formulae given below, without for all that limiting the invention to the substrates defined by the formulae given.

In accordance with the process of the invention, a substituted phenol compound of formula (I) is carboxylated, in a first stage, by reaction of the said substituted phenol compound, in the salified form, with carbon dioxide.

The substituted phenol compounds thus take part in the process of the invention in the salified form. They are preferentially salts of metal elements from group (Ia) of the periodic classification.

For the definition of the elements, reference is made below to the periodic classification of the elements published in Bulletin de la Société Chimique de France, No. 1 (1966).

From a practical and economic viewpoint, sodium or potassium salts are used.

In accordance with the process of the invention, the substituted phenol compound in the salified form and carbon dioxide are reacted.

4

Use may be made of a salified form of a substituted phenol compound prepared at the time of use but it is also possible to prepare it in situ by reacting the substituted phenol compound with a base.

A base, which can be inorganic or organic, is thus involved in the process of the invention.

A strong base is preferentially chosen, that is to say a base having a $pK_b$ greater than 12, the $pK_b$ being defined as the cologarithm of the dissociation constant of the base measured, in aqueous medium, at 25° C.

Inorganic bases, such as alkali metal salts, preferably an alkali metal hydroxide which can be sodium or potassium hydroxide, or an alkali metal carbonate, preferably potassium carbonate, are particularly well suited to the implementation of the process of the invention.

It is also possible to use a quaternary ammonium hydroxide.

Use is preferentially made, as examples of quaternary ammonium hydroxide, of tetraalkylammonium or trialkylbenzylammonium hydroxides in which the identical or different alkyl radicals represent a linear or branched alkyl chain having from 1 to 12 carbon atoms, preferably from 1 to 6 carbon atoms.

Tetramethylammonium hydroxide, tetraethylammonium hydroxide or tetrabutylammonium hydroxide is preferentially chosen.

It is also possible, according to the invention, to resort to trialkylbenzylammonium hydroxides and in particular to trimethylbenzylammonium hydroxide.

For economic reasons, sodium hydroxide or potassium carbonate is preferentially chosen from all the bases.

The concentration of the starting basic solution is not critical. The alkali metal hydroxide solution used generally has a concentration of between 10 and 50% by weight.

The amount of base introduced into the reaction mixture takes into account the amount necessary to salify the hydroxyl functional group of the substituted phenol compound.

If the said compound has salifiable functional groups other than the hydroxyl group, the amount of base necessary to salify all the salifiable functional groups is therefore introduced.

The amount of base, expressed with respect to the substituted phenol compound, generally varies between 90% and 120% of the stoichiometric amount.

The substituted phenol compound is prepared in the salified form by reacting it with the base at a temperature advantageously of between 25° C. and 100° C.

Before introducing the carbon dioxide, the water formed during the salification reaction is removed by distillation at atmospheric pressure or under a reduced pressure of between 1 mm of mercury and atmospheric pressure or by drying. When there is no longer water in the mixture, the carbon dioxide is introduced.

Another alternative form of the process of the invention comprises the additional use of an anhydrous alkali metal carbonate, preferably anhydrous potassium carbonate, which makes it possible to avoid the stage of removal of water (for example, from 5 to 100 mol % of substituted phenol compound).

The amount of carbon dioxide to be used, expressed by the molar ratio between the carbon dioxide and the substituted phenol compound, varies between 1 and 100 and more preferentially between 1 and 2.

The process of the invention is advantageously carried out at a temperature of between 150° C. and 250° C., preferably between 160° C. and 200° C.

It is generally implemented at atmospheric pressure, the carbon dioxide being bubbled into the reaction mixture, which is kept stirring.

It is also possible to carry out the reaction under a carbon dioxide pressure varying between atmospheric pressure and approximately 100 bar. A pressure between 1 and 20 is preferred.

A preferred practical embodiment of the invention comprises the use of the substituted phenol compound and the base, the removal of the water, if necessary, by distillation and then the introduction of the carbon dioxide. It is a solid/gas reaction.

At the end of the reaction, the substituted phenol compound, carrying a carboxylate group in the 6 position, is then recovered and is dissolved in water at a concentration varying between 5 and 50% by weight.

The solution is brought to a pH of between approximately 6 and 10, preferably in the region of 7, by addition of an acid.

Any acid may be used but, for economic reasons, it is preferable to use conventional inorganic acids, preferably hydrochloric acid or sulphuric acid. The concentration of the acid used is not critical. It preferably corresponds to the concentration of the commercial form, for example 37% by weight for hydrochloric acid and 92 or 96% for sulphuric acid.

A two-phase mixture is then obtained, composed of an organic phase comprising the unreacted substituted phenol compound and, on the other hand, an aqueous phase comprising the desired product, namely the salt of 2-hydroxybenzoic acid substituted at least in the 3 position by an alkoxy group which is represented by the formula (II) in which $Z_1$, $Z_2$ and $Z_3$ have the meanings given above and M represents a hydrogen atom and/or a metal cation from group (Ia).

It is subsequently known simply as "hydroxybenzoic acid salt".

The two phases are separated and the aqueous phase is collected.

It should be noted that it will not be departing from the scope of the present invention to start from the hydroxybenzoic acid salt of formula (II) prepared at the time of use.

In a following stage, a hydroxymethylation reaction in the position para to the OH group is carried out by reaction of the salt of the acid obtained above with formaldehyde, optionally in the presence of a base.

It is possible to use formaldehyde or any generator of formaldehyde, such as, for example, trioxane or paraformaldehyde used in the form of linear polyformaldehydes, in which the degree of polymerization is immaterial, preferably having a number of ($CH_2O$) units of between 8 and 100 units.

The said reactant is generally used in the form of an aqueous solution having a concentration of less than 50% by weight, preferably of between 20 and 50% by weight.

The amount of formaldehyde, expressed as moles of formaldehyde per mol of hydroxybenzoic acid salt, can vary within wide limits. The formaldehyde/hydroxybenzoic acid salt molar ratio advantageously lies between 0.5 and 3.0.

It is possible to carry out the reaction in the presence of a base. The bases mentioned above are entirely well suited.

The amount of base used, expressed by the ratio of the number of moles of base to the number of moles of hydroxybenzoic acid salt, can vary between 0 and 2 and preferably between 0 and 1.1.

The base can be used without distinction in the solid form or as an aqueous solution.

The temperature of the reaction can vary from 50° C. to 100° C. and preferably from 60° C. to 80° C.

The process is preferably carried out under the autogenous pressure of the reactants in order to avoid possible losses of paraformaldehyde, which may be gaseous at the implementational temperatures.

It is preferable to carry out the reaction under a controlled atmosphere of inert gases, such as nitrogen or rare gases, for example argon.

The duration of the reaction can be highly variable. It most often lies between 30 minutes and 24 hours, preferably between 4 hours and 8 hours.

From a practical viewpoint, the reaction is easily carried out by charging the hydroxybenzoic acid salt and the formaldehyde and optionally a base to the equipment and by then bringing the reaction mixture, with stirring, to the desired temperature for the duration necessary for completion of the reaction.

The order of introduction of the reactants is not critical and can therefore be different.

At the end of the reaction, a 2-hydroxybenzoic acid which is hydroxymethylated in the 5 position and which is substituted at least in the 3 position by an alkoxy group is obtained which preferentially corresponds to the formula (III) in which $Z_1$, $Z_2$ and $Z_3$ have the meanings given above and M represents a hydrogen atom and/or a metal cation from group (Ia).

According to a preferred alternative form of the process of the invention, the compound obtained is not separated but is directly oxidized.

A preferred method of oxidation of the invention, which constitutes another subject of the present invention, comprises the oxidation of 2-hydroxybenzoic acid which is hydroxymethylated in the 5 position and which is substituted at least in the 3 position by an alkoxy group, in the liquid phase, using molecular oxygen or a gas containing it, the oxidation being carried out in aqueous medium containing an alkaline agent, in the presence of a catalyst based on platinum or on palladium, optionally in the presence of a cocatalyst based on a bismuth derivative.

As regards the noble metals used for catalysing the reaction, in this case platinum and palladium, they can have various forms such as, for example: platinum black, palladium black, platinum oxide, palladium oxide or the noble metal itself deposited on various supports, such as carbon black, calcium carbonate, activated aluminas and silicas or equivalent materials. Catalytic bodies based on carbon black are particularly suitable.

The amount of this catalyst to be used, expressed as weight of platinum or palladium with respect to that of the hydroxymethylated 2-hydroxybenzoic acid, can vary from 0.01 to 4% and preferably from 0.04 to 2%.

A cocatalyst can be used and, more particularly, use is generally made of an inorganic or organic bismuth derivative in which the bismuth atom has an oxidation number greater than zero, for example equal to 2, 3, 4 or 5. The residue combined with the bismuth is not critical, as soon as it satisfies this condition. The cocatalyst can be soluble or insoluble in the reaction mixture.

Compounds illustrative of cocatalysts which can be used in the process according to the present invention are: bismuth oxides, bismuth hydroxides, salts of inorganic hydracids, such as bismuth chloride, bromide, iodide, sulphide, selenide and telluride, salts of inorganic oxyacids, such as bismuth sulphide, sulphate, nitrite, nitrate, phosphite, phosphate, pyrophosphate, carbonate, perchlorate, antimonate, arsenate, selenite and selenate, or salts of oxyacids derived from transition metals, such as bismuth vanadate, niobate, tantalate, chromate, molybdate, tungstate and permanganate.

Salts of aliphatic or aromatic organic acids, such as bismuth acetate, propionate, benzoate, salicylate, oxalate, tartrate, lactate and citrate or phenoxides, such as bismuth gallate and pyrogallate, are also other appropriate compounds. These salts and phenoxides can also be bismuthyl salts.

Use may be made, as other inorganic or organic compounds, of binary combinations of bismuth with elements such as phosphorus and arsenic; heteropolyacids containing bismuth, and their salts; aliphatic and aromatic bismuthines are also suitable.

Mention may be made, as specific examples, of:

- as oxides: BiO, $Bi_2O_3$, $Bi_2O_4$ or $Bi_2O_5$,
- as hydroxides: $Bi(OH)_3$,
- as salts of inorganic hydracids: bismuth chloride $BiCl_3$, bismuth bromide $BiBr_3$, bismuth iodide $BiI_3$, bismuth sulphide $Bi_2S_3$, bismuth selenide $Bi_2Se_3$ or bismuth telluride $Bi_2Te_3$,
- as salts of inorganic oxyacids: basic bismuth sulphite $Bi_2(SO_3)_3.Bi_2O_3.5H_2O$, neutral bismuth sulphate $Bi_2(SO_4)_3$, bismuthyl sulphate $(BiO)HSO_4$, bismuthyl nitrite $(BiO)NO_2.0.5H_2O$, neutral bismuth nitrate $Bi(NO_3)_3.5H_2O$, bismuth magnesium nitrate $2Bi(NO_3)_3.3Mg(NO_3)_2.24H_2O$, bismuthyl nitrate $(BiO)NO_3$, bismuth phosphite $Bi_2(PO_3H)_3.3H_2O$, neutral bismuth phosphate $BiPO_4$, bismuth pyrophosphate $Bi_4(P_2O_7)_3$, bismuthyl carbonate $(BiO)_2CO_3.0.5H_2O$, neutral bismuth perchlorate $Bi(ClO_4)_3.5H_2O$, bismuthyl perchlorate $(BiO)ClO_4$, bismuth antimonate $BiSbO_4$, neutral bismuth arsenate $Bi(AsO_4)_3$, bismuthyl arsenate $(BiO)AsO_4.5H_2O$ or bismuth selenite $Bi_2(SeO_3)_3$,
- as salts of oxyacids derived from transition metals: bismuth vanadate $BiVO_4$, bismuth niobate $BiNbO$, bismuth tantalate $BiTaO_4$, neutral bismuth chromate $Bi_2(CrO_4)$, bismuthyl dichromate $(BiO)_2Cr_2O_7$, acid bismuthyl chromate $H(BiO)CrO_4$, bismuthyl potassium chromate $K(BiO)CrO_4$, bismuth molybdate $Bi_2(MoO_4)_3$, bismuth tungstate $Bi_2(WO_4)_3$ bismuth sodium molybdate $NaBi(Mo_4)_2$ or basic bismuth permanganate $Bi_2O_2(OH)MnO_4$,
- as salts of aliphatic or aromatic organic acids: bismuth acetate $Bi(C_2H_3O_2)_3$, bismuthyl propionate $(BiO)C_3H_5O_2$, basic bismuth benzoate $C_6H_5CO_2Bi(OH)_2$, bismuthyl salicylate $C_6H_4CO_2(BiO)(OH)$, bismuth oxalate $(C_2O_4)_3Bi_2$, bismuth tartrate $Bi_2(C_4H_4O_6)_3.6H_2O$, bismuth lactate $(C_6H_9O_5)OBi.7H_2O$ or bismuth citrate $C_6H_5O_7Bi$,
- as phenoxides: basic bismuth gallate $C_7H_7O_7Bi$ or basic bismuth pyrogallate $C_6H_3(OH)_2(OBi)(OH)$.

As other inorganic or organic compounds which are also suitable: bismuth phosphide BiP, bismuth arsenide $Bi_3As_4$, sodium bismuthate $NaBiO_3$, bismuth-thiocyanic acids $H_2[Bi(CNS)_5]$ or $H_3[Bi(CNS)_6]$ and their sodium and potassium salts, trimethylbismuthine $Bi(CH_3)_3$ or triphenylbismuthine $Bi(C_6H_5)_3$.

The bismuth derivatives which are preferably used in carrying out the process according to the invention are: bismuth oxides, bismuth hydroxides, bismuth or bismuthyl salts of inorganic hydracids, bismuth or bismuthyl salts of inorganic oxyacids, bismuth or bismuthyl salts of aliphatic or aromatic organic acids and bismuth or bismuthyl phenoxides.

A group of cocatalysts which are particularly well suited to carrying out the invention is composed of: bismuth oxides $Bi_2O_3$ and $Bi_2O_4$, bismuth hydroxide $Bi(OH)_3$, neutral bismuth sulphate $Bi_2(SO_4)_3$, bismuth chloride $BiCl_3$, bismuth bromide $BiBr_3$, bismuth iodide $BiI_3$, neutral bismuth nitrate, $Bi(NO_3)_3.5H_2O$, bismuthyl nitrate $BiO(NO_3)$, bismuthyl carbonate $(BiO)_2CO_3.0.5H_2O$, bismuth acetate $Bi(C_2H_3O_2)_3$ or bismuthyl salicylate $C_6H_4CO_2(BiO)(OH)$.

The amount of cocatalyst used, expressed by the amount of metallic bismuth contained in the cocatalyst with respect to the weight of the noble metal used, can vary within wide limits. For example, this amount can be as small as 0.1% and can reach the weight of noble metal used and even exceed it without disadvantage.

More particularly, this amount is chosen so that it introduces into the oxidation mixture from 10 to 900 ppm by weight of metallic bismuth with respect to the hydroxymethylated 2-hydroxybenzoic acid. In this respect, larger amounts of cocatalyst, of the order of 900 to 1500 ppm, can naturally be used but without significant additional advantage.

According to the process of the invention, the oxidation is carried out in an aqueous medium containing an alkaline agent in solution. In this respect, sodium or potassium hydroxide is generally used as alkaline agent. The proportion of inorganic base to be used is between 0.5 and 3 mol of sodium or potassium hydroxide with respect to the hydroxymethylated 2-hydroxybenzoic acid.

The concentration of the hydroxymethylated 2-hydroxybenzoic acid in the aqueous alkaline agent solution must preferably be such that any precipitation is avoided and a homogeneous solution is retained.

The concentration by weight of the hydroxymethylated 2-hydroxybenzoic acid in the aqueous medium is usually between 1% and 60%, preferably between 2% and 30%.

A way of carrying out the process in practice consists in bringing the aqueous solution containing the hydroxymethylated 2-hydroxybenzoic acid to be oxidized, the alkaline agent, the catalyst based on platinum or on palladium and, optionally, the cocatalyst based on a bismuth derivative, according to the proportions shown above, into contact with molecular oxygen or a gas containing it, for example air.

The process is carried out at atmospheric pressure but it is also possible, if appropriate, to carry out the process under pressure between 1 and 20 bars.

The mixture is then stirred at the desired temperature until an amount of oxygen corresponding to that necessary to convert the alcohol functional group to an aldehyde functional group has been consumed. The progress of the reaction is therefore monitored by measuring the amount of oxygen absorbed.

The reaction temperature to be adopted varies according to the thermal stability of the products to be prepared.

The reaction is generally carried out in a temperature range from 50° C. to 100° C., preferably from 60° C. to 80° C.

At the end of the reaction, which preferably lasts between 30 minutes and 2 hours, the 2-hydroxybenzoic acid is recovered which is formylated in the 5 position and which is substituted at least in the 3 position by an alkoxy group and which preferentially corresponds to the formula (IV).

The catalyst, after cooling, if it takes place, is then separated from the reaction mixture, for example by filtration.

In the last stage of the process of the invention, a decarboxylation reaction is carried out.

To do this, the resulting liquid is acidified by addition of a proton acid of inorganic origin, preferably hydrochloric acid or sulphuric acid, until a pH less than or equal to 3, preferably between 0 and 3, is obtained.

The reaction mixture is heated at a temperature varying, for example, between 120° C. and 350° C. and preferably between 150° C. and 220° C.

The process is preferably carried out under the autogenous pressure of the reactants.

At the end of the reaction, the reaction mixture is cooled to between 20° C. and 80° C.

A two-phase mixture is obtained which is composed, on the one hand, of an organic phase comprising the 4-hydroxybenzaldehyde substituted at least in the 3 position by an alkoxy group and preferentially corresponding to the formula (V) and optionally the starting substrate of formula (I) and, on the other hand, of a saline aqueous phase.

The organic and aqueous phases are separated and the substituted 4-hydroxybenzaldehyde is recovered from the organic phase according to conventional separation techniques, preferably by distillation.

As mentioned above, the process of the invention is particularly well suited to the preparation of vanillin and of ethyl vanillin.

Examples of the implementation of the invention are given below. These examples are given by way of illustration and without implied limitation.

EXAMPLES

Example 1

1—Carboxylation of potassium quaiacolate under $CO_2$ pressure.

224 g (1.81 mol) of guaiacol are charged to a 500 ml Burton Corbelin reactor made of hastelloy $B_2$ and equipped with a turbine mixer.

31.5 g (228 mmol) of potassium carbonate are added.

The reactor is purged with a stream of $CO_2$. A slight exotherm is recorded as taking place.

The reaction mixture is heated at 170° C. for 7 hours, while maintaining the $CO_2$ pressure at 20 bars.

After cooling the reactor to room temperature, 200 ml of water are added.

A 5N hydrochloric acid solution is run in until a pH of approximately 7.0 is obtained. Phase separation takes place.

The organic phase, composed essentially of guaiacol, is separated by settling.

The aqueous phase is acidified to pH 1 with hydrochloric acid. Precipitation of orthovanillic acid takes place.

Separation is carried out by filtration. The product obtained is washed with water and dried at 40° C. under a reduced pressure of 20 mm of mercury.

38 g of ortho-vanillic acid are recovered, assaying at 96% by weight.

The yield is 96% with respect to the potassium carbonate.

2—ortho-Vanillic acid/paraformaldehyde condensation.

14.66 g of a 30% aqueous sodium hydroxide solution (0.11 mol) are added, with stirring and while heating, to a suspension of 16.8 g (0.1 mol) of ortho-vanillic acid in 16.72 g of water.

When the mixture is homogeneous and at a temperature of 70° C., 3 g of paraformaldehyde (0.1 mol) are added.

After stirring for 6 hours at 70° C., the purple solution obtained is quantitatively determined by high performance liquid chromatography.

The results obtained are as follows:

DC (o-vanillic acid)=no. of moles of o-vanillic acid converted/no. of moles of o-vanillic acid used=42.5%

RY (3-methoxy-5-hydroxymethylsalicylic acid)=no. of moles of 3-methoxy-5-hydroxymethylsalicylic acid formed/no. of moles of o-vanillic acid used=29.95%

CY=no. of moles of 3-methoxy-5-hydroxymethylsalicylic acid formed/no. of moles of o-vanillic acid converted= 70.5%.

3—Oxidation.

1.63 g of 2.5% platinum-on-charcoal (0.2 mol %) and then 140 mg of bismuth sulphate (0.2 mol %) are added to the above solution.

The temperature is adjusted to 65° C. and the pH to 12. The latter will be maintained at this value during the reaction by addition of 30% sodium hydroxide.

Oxygen is conveyed into the reactor with strong agitation at a flow rate of 1.5 l/h.

After 3 hours, 0.815 g of platinum-on-charcoal is added and the reaction is continued for an additional 3 hours.

At this time, quantitative determination of the reaction mixture by high performance liquid chromatography gives:

DC (3-methoxy-5-hydroxymethylsalicylic acid)=no. of moles of 3-methoxy-5-hydroxymethylsalicylic acid converted/no. of moles of 3-methoxy-5-hydroxymethylsalicylic acid used=100%

RY (5-carboxyvanillin)=no. of moles of 5-carboxyvanillin formed/no. of moles of 3-methoxy-5-hydroxymethylsalicylic acid used=59%.

4—Decarboxylation.

The reaction mixture resulting from the oxidation is diluted with 100 ml of water and is then charged to a Burton Corbelin reactor made of hastelloy $B_2$.

A 2N sulphuric acid solution is run in until a pH of approximately 1.9 is obtained.

The reactor is purged under a stream of nitrogen and heating is then carried out for 30 min at 200° C.

Cooling is rapidly carried out by a stream of cold water.

The reaction mixture is diluted with acetonitrile and is then quantitatively determined by high performance liquid chromatography.

The results obtained are as follows:

DC (5-carboxyvanillin)=no. of moles of 5-carboxyvanillin converted/no. of moles of 5-carboxyvanillin used=100%.

CY (vanillin)=no. of moles of vanillin formed/no. of moles of 5-carboxyvanillin converted=99.4%

RY (vanillin/o-vanillic acid)=no. of moles of vanillin formed/no. of moles of o-vanillic acid used=27.4%.

Examples 2 to 4

A series of decarboxylation tests on 3-carboxy-4-hydroxy-5-methoxybenzaldehyde is carried out.

The following are charged to a 50 ml Burton Corbelin reactor made of hastelloy $B_2$ and equipped with a turbine mixer: 0.246 g (1.26 mmol) of 5-carboxyvanillin and 20 ml of a mixture of acetic acid and water (50/50 by volume) in Example 2, 20 ml of water in Example 3 and 20 ml of a sulphuric acid solution (5 mmol/l) in Example 4.

The reactor is purged under a stream of nitrogen.

Heating is carried out for 20 min. at 160° C. in Examples 2 and 3 and 200° C. in Example 4.

The reaction mixture is quantitatively determined by high performance liquid chromatography after dilution with acetonitrile: Lichro Cart RP 18–5 µm–250/4 mm column marketed by Merck; eluent: 800 ml $H_2O$/200 ml $CH_3CN$/3.5 ml $H_3PO_4$; flow rate: 1 ml.mn$^{-1}$; UV detection: 240 µm; room temperature.

The results are recorded in the following Table (I):

TABLE (I)

| Example Ref. | Nature of the solvent | Temperature (°C.) | Duration (h) | DC (5-carboxy-vanillin) (%) | CY (vanillin) (%) |
|---|---|---|---|---|---|
| 2 | CH₃COOH/H₂O | 160 | 7 h 05 | 89.6 | 95.1 |
| 3 | H₂O | 160 | 6 h 35 | 96.5 | 91.1 |
| 4 | H₂SO₄ | 200 | 0 h 20 | 98.9 | 98.4 |

What is claimed is:

1. A process for the preparation of a substituted 4-hydroxybenzaldehyde, substituted at least in the 3 position by an alkoxy group, comprising the steps of subjecting a substituted phenol compound, substituted at least in the 2 position by an alkoxy group and in which the 4 and 6 positions are free, to a first stage of carboxylation in the 6 position, then to a stage of hydroxymethylation in the 4 position, followed by a stage of oxidation of the hydroxymethyl group to a formyl group, and finally to a last decarboxylation stage.

2. A process according to claim 1, wherein the substituted phenol compound corresponds to the general formula (I):

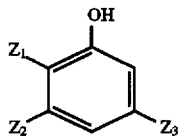

wherein:

$Z_1$ represents a linear or branched alkoxy radical having from 1 to 12 carbon atoms; and $Z_2$ and $Z_3$, which are identical or different, is selected from the group consisting of a hydrogen atom, a linear or branched alkyl radical having from 1 to 12 carbon atoms, a linear or branched alkenyl radical having from 2 to 12 carbon atoms, a linear or branched alkoxy radical having from 1 to 12 carbon atoms, a phenyl radical, and a halogen atom.

3. A process according to claim 2, wherein:

$Z_1$ is methoxy, ethoxy, propoxy, isopropoxy, butoxy, isobutoxy, sec-butoxy or tert-butoxy; and $Z_2$ and $Z_3$, which are identical or different, is a hydrogen atom, methyl, ethyl, propyl, isopropyl, butyl, isobutyl, sec-butyl or tert-butyl, vinyl or allyl, methoxy, ethoxy, propoxy, isopropoxy, butoxy, isobutoxy, sec-butoxy, tert-butoxy, fluorine, chlorine or bromine atom.

4. A process according to claim 2, wherein the substituted phenol compound corresponds to the formula (I) in which $Z_1$ represents a linear or branched alkoxy radical having from 1 to 6 carbon atoms; and $Z_2$ and $Z_3$ represent a hydrogen atom.

5. A process according to claim 1, wherein the substituted phenol compound is guaiacol or 2-ethoxyphenol.

6. A process according to claim 1, wherein, in the first stage, the substituted phenol compound is carboxylated by reaction of said compound in the salified form with carbon dioxide.

7. A process according to claim 6, wherein the substituted phenol compound in the salified form is in the form of a salt of a metal element from group (Ia) of the periodic classification.

8. A process according to claim 7, wherein the metal element is sodium or potassium.

9. A process according to claim 7, wherein the substituted phenol compound in the salified form is prepared by reacting the said phenol compound with a base or a quaternary ammonium hydroxide, and by then removing the water formed during the salification reaction or by addition of an anhydrous alkaline carbonate.

10. A process according to claim 6, wherein the temperature at which the carboxylation takes place is between 150° C. and 250° C.

11. A process according to claim 6, wherein the carbon dioxide pressure varies between atmospheric pressure and about 100 bar.

12. A process according to claim 6, wherein said first stage comprises the use of the substituted phenol compound and the base, the removal of the water and then the introduction of the carbon dioxide.

13. A process for the preparation of a 2-hydroxybenzoic acid which is hydroxymethylated in the 5 position and which is substituted at least in the 3 position by an alkoxy group comprising the reaction of a substituted 2-hydroxybenzoic acid, substituted at least in the 3 position by an alkoxy group, with formaldehyde or a formaldehyde generator, optionally in the presence of a base.

14. A process according to claim 13, wherein the substituted 2-hydroxybenzoic acid, substituted at least in the 3 position by an alkoxy group, corresponds to the general formula (II):

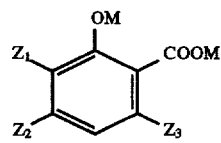

wherein:

$Z_1$ represents a linear or branched alkoxy radical having from 1 to 12 carbon atoms;

$Z_2$ and $Z_3$, which are identical or different, is selected from the group consisting of a hydrogen atom, a linear or branched alkyl radical having from 1 to 12 carbon atoms, a linear or branched alkenyl radical having from 2 to 12 carbon atoms, a linear or branched alkoxy radical having from 1 to 12 carbon atoms, a phenyl radical, and a halogen atom; and M represents a hydrogen atom and/or a metal cation from group (Ia).

15. A process according to claim 13, wherein the formaldehyde generator is trioxane or paraformaldehyde used in the form of a linear polyformaldehyde.

16. A process according to claim 15, wherein the polyformaldehyde has a number of ($CH_2O$) units of between 8 and 100.

17. A process according to claim 15, wherein the formaldehyde/hydroxybenzoic acid salt molar ratio lies between 0.5 and 3.0.

18. A process according to claim 13, wherein the temperature of the reaction varies from 50° C. to 100° C.

19. A process for the preparation of a 2-hydroxybenzoic acid which is formylated in the 5 position and which is substituted at least in the 3 position by an alkoxy group, wherein it comprises the oxidation of 2-hydroxybenzoic acid which is hydroxymethylated in the 5 position and which is substituted at least in the 3 position by an alkoxy group, in the liquid phase, using molecular oxygen or a gas containing it, the oxidation being carried out in aqueous reaction medium containing an alkaline agent, in the presence of a catalyst based on platinum or on palladium, optionally in the presence of a cocatalyst based on a bismuth derivative.

20. A process according to claim 19, wherein the 2-hydroxybenzoic acid which is hydroxymethylated in the 5 position and which is substituted at least in the 3 position by an alkoxy group corresponds to the general formula (III):

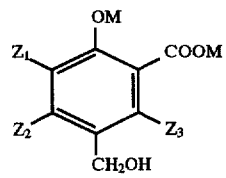

wherein:

$Z_1$ represents a linear or branched alkoxy radical having from 1 to 12 carbon atoms;

$Z_2$ and $Z_3$, which are identical or different, is selected from the group consisting of a hydrogen atom, a linear or branched alkyl radical having from 1 to 12 carbon atoms, a linear or branched alkenyl radical having from 2 to 12 carbon atoms, a linear or branched alkoxy radical having from 1 to 12 carbon atoms, a phenyl radical, and a halogen atom; and M represents a hydrogen atom and/or a metal cation from group (Ia).

21. A process according to claim 19, wherein said catalyst is selected from the group consisting of platinum black, palladium black, platinum oxide and palladium oxide.

22. A process according to claim 21, wherein the amount of the catalyst, expressed as weight of platinum or palladium with respect to that of the hydroxymethylated 2-hydroxybenzoic acid, is from 0.01 to 4%.

23. A process according to claim 19, wherein said cocatalyst is an inorganic or organic bismuth derivative in which the bismuth atom has an oxidation number greater than zero.

24. A process according to claim 23, wherein the bismuth derivative is selected from the group consisting of bismuth oxides, bismuth hydroxides, bismuth or bismuthyl salts of inorganic hydracids, bismuth or bismuthyl salts of inorganic oxyacids, bismuth or bismuthyl salts of aliphatic or aromatic organic acids and bismuth or bismuthyl phenoxides.

25. A process according to claim 24, wherein the bismuth derivative is selected from the group consisting of bismuth oxides $Bi_2O_3$ and $Bi_2O_4$, bismuth hydroxide $Bi(OH)_3$, bismuth chloride $BiCl_3$, bismuth bromide $BiBr_3$, bismuth iodide $BiI_3$, neutral bismuth sulphate $Bi_2(SO_4)_3$, neutral bismuth nitrate $Bi(NO_3)_3.5H_2O$, bismuthyl nitrate $BiO(NO_3)$, bismuthyl carbonate $(BiO)_2CO_3.0.5H_2O$, bismuth acetate $Bi(C_2H_3O_2)_3$ and bismuthyl salicylate $C_6H_4CO_2(BiO)OH$.

26. A process according to claim 24, wherein the amount of cocatalyst used is chosen so that it introduces into the mixture: on the one hand, at least 0.1% by weight of metallic bismuth with respect to the weight of catalyst used and, on the other hand, from 10 to 800 ppm by weight of metallic bismuth with respect to the hydroxymethylated 2-hydroxybenzoic acid.

27. A process according to claim 19, wherein the oxidation reaction is carried out in an aqueous medium containing from 0.5 to 3 mol of sodium or potassium hydroxide with respect to the hydroxymethylated 2-hydroxybenzoic acid.

28. A process according to claim 19, wherein the oxidation reaction is carried out at a temperature ranging from 50° C. to 100° C.

29. A process according to claim 28, wherein the reaction medium is cooled and the catalyst is separated.

30. A process according to claim 19, wherein the 2-hydroxybenzoic acid which is formylated in the 5 position and which is substituted at least in the 3 position by an alkoxy group, is decarboxylated.

31. A process according to claim 30, wherein the 2-hydroxybenzoic acid which is formylated in the 5 position and which is substituted at least in the 3 position by an alkoxy group corresponds to the general formula (IV):

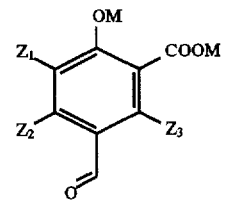

wherein:

$Z_1$ represents a linear or branched alkoxy radical having from 1 to 12 carbon atoms;

$Z_2$ and $Z_3$, which are identical or different, is selected from the group consisting of a hydrogen atom, a linear or branched alkyl radical having from 1 to 12 carbon atoms, a linear or branched alkenyl radical having from 2 to 12 carbon atoms, a linear or branched alkoxy radical having from 1 to 12 carbon atoms, a phenyl radical, and a halogen atom; and M represents a hydrogen atom and/or a metal cation from group (Ia).

32. A process according to claim 30, wherein said acid is decarboxylated by addition of a proton acid of inorganic origin until a pH less than or equal to 3.

33. A process according to claim 30, wherein the reaction medium is heated at a temperature varying between 120° C. and 350° C. and preferably between 150° C. and 220° C. and, after cooling, in that the substituted 4-hydroxybenzaldehyde, substituted at least in the 3 position by an alkoxy group, corresponding to the formula (V):

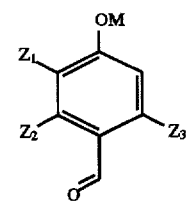

wherein:

$Z_1$ represents a linear or branched alkoxy radical having from 1 to 12 carbon atoms;

$Z_2$ and $Z_3$, which are identical or different, is selected from the group consisting of a hydrogen atom, a linear or branched alkyl radical having from 1 to 12 carbon atoms, a linear or branched alkenyl radical having from 2 to 12 carbon atoms, a linear or branched alkoxy radical having from 1 to 12 carbon atoms, a phenyl radical, and a halogen atom; and M represents a hydrogen atom and/or a metal cation from group (Ia), is separated.

34. A process according to claim 20, wherein:

$Z_1$ is methoxy, ethoxy, propoxy, isopropoxy, butoxy, isobutoxy, sec-butoxy or tert-butoxy;

$Z_2$ and $Z_3$, which are identical or different, is a hydrogen atom, methyl, ethyl, propyl, isopropyl, butyl, isobutyl, sec-butyl or tert-butyl, vinyl or allyl, methoxy, ethoxy, propoxy, isopropoxy, butoxy, isobutoxy, sec-butoxy, tert-butoxy, fluorine, chlorine or bromine atom; and M represents a hydrogen atom and/or a metal cation from group (Ia).

35. A process according to claim 34, wherein $Z_1$ is methoxy or ethoxy radical; and $Z_2$ and $Z_3$ is a hydrogen atom.

36. A method of using a 2-Hydroxybenzoic acid hydroxymethylated in the 5 position and substituted at least in the 3 position by an alkoxy group as an intermediary product for the preparation of a 4-hydroxybenzaldehyde substituted in the 5 position by an alkoxy group.

37. A method according to claim 36, wherein the said 2-Hydroxybenzoic acid hydroxymethylated in the 5 position and substituted at least in the 3 position by an alkoxy group corresponds to the general formula (III):

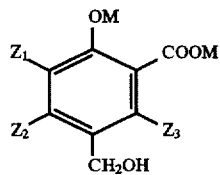

wherein:

$Z_1$ represents a linear or branched alkoxy radical having from 1 to 12 carbon atoms;

$Z_2$ and $Z_3$, which are identical or different, is selected from the group consisting of a hydrogen atom, a linear or branched alkyl radical having from 1 to 12 carbon atoms, a linear or branched alkenyl radical having from 2 to 12 carbon atoms, a linear or branched alkoxy radical having from 1 to 12 carbon atoms, a phenyl radical, and a halogen atom; and M represents a hydrogen atom and/or a metal cation from group (Ia).

38. A method according to claim 37, wherein:

$Z_1$ is methoxy, ethoxy, propoxy, isopropoxy, butoxy, isobutoxy, sec-butoxy or tert-butoxy;

$Z_2$ and $Z_3$, which are identical or different, is a hydrogen atom, methyl, ethyl, propyl, isopropyl, butyl, isobutyl, sec-butyl or tert-butyl, vinyl or allyl, methoxy, ethoxy, propoxy, isopropoxy, butoxy, isobutoxy, sec-butoxy, tert-butoxy, fluorine, chlorine or bromine atom; and M represents a hydrogen atom and/or a metal cation from group (Ia).

39. A method according to claim 38, wherein $Z_1$ is methoxy or ethoxy radical; and $Z_2$ and $Z_3$ is a hydrogen atom.

* * * * *